United States Patent
Loozen et al.

(10) Patent No.: US 7,528,123 B1
(45) Date of Patent: May 5, 2009

(54) ESTROGENIC ESTRA-1,3,5(10)-TRIENES WITH DIFFERENTIAL EFFECTS ON THE ALPHA AND BETA ESTROGEN RECEPTORS, HAVING A LINEAR HYDROCARBON CHAIN OF FROM 5-9 CARBON ATOMS IN POSITION 11

(75) Inventors: Hubert Jan Jozef Loozen, Meerhoek (NL); Wilhelmus Gerardus Eduardus Joseph Schoonen, Parklaan (NL)

(73) Assignee: N.V. Organon, Oss (NL)

( * ) Notice: Subject to any disclaimer, the term of this patent is extended or adjusted under 35 U.S.C. 154(b) by 0 days.

(21) Appl. No.: 09/831,954

(22) PCT Filed: Nov. 18, 1999

(86) PCT No.: PCT/EP99/09053

§ 371 (c)(1),
(2), (4) Date: Jun. 25, 2001

(87) PCT Pub. No.: WO00/31112

PCT Pub. Date: Jun. 2, 2000

(30) Foreign Application Priority Data

Nov. 20, 1998 (EP) .................................. 98203914

(51) Int. Cl.
*A61K 31/56* (2006.01)
*C07J 1/00* (2006.01)
(52) U.S. Cl. ....................... 514/178; 514/179; 514/181; 514/182; 552/623; 552/642
(58) Field of Classification Search ................. 514/169, 514/178, 179, 181, 182
See application file for complete search history.

(56) References Cited

U.S. PATENT DOCUMENTS 3,755,301 A * 8/1973 Baran et al.

FOREIGN PATENT DOCUMENTS

| DE | 41 32 182 | 3/1993 |
| EP | 0 798 378 | 10/1997 |
| WO | WO 93 13123 | 7/1993 |

OTHER PUBLICATIONS

Lobaccaro, C. et al., "Steroidal Affinity Labels of the Estrogen Receptor. 3. Estradiol 11.beta.-n-Alkyl Derivatives Bearing A Terminal Electrophilic Group: Anti-Estrogenic and Cytotoxic Properties" Journal of Medicinal Chemistry, vol. 40, No. 14, Jul. 4, 1997, p. 2217-2227.
Napolitano, E. et al., "11.beta.-Substituted Estradiol Derivatives. 2. Potential Carbon-11-and Iodine-Labeled Probes for the Estrogen Receptor" Journal of Medicinal Chemistry, col. 38, No. 14, Jul. 7, 1995, p. 2774-2779.
Mosselman et al., "Erβ identification and characterization of a novel human estrogen Receptor," *FEBS Letters 392* (1996) 49-53.

* cited by examiner

*Primary Examiner*—Sreeni Padmanabhan
*Assistant Examiner*—Renee Claytor
(74) *Attorney, Agent, or Firm*—Susan Hess

(57) ABSTRACT

Disclosed is a novel class of steroid compounds based on estradiol, and carrying an 11β-substitution. Said substitution is a hydrocarbon group which may be linear or branched, provided that it comprises, as the longest chain on carbon atom no. 11 of the steroid skeleton, one single linear chain having a length of from 5 to 9 carbon atoms, wherein said chain may be saturated or unsaturated. The resulting compounds have a desirable mixed agonist/antagonist profile for estrogen receptor α and estrogen receptor β.

4 Claims, No Drawings

ESTROGENIC ESTRA-1,3,5(10)-TRIENES WITH DIFFERENTIAL EFFECTS ON THE ALPHA AND BETA ESTROGEN RECEPTORS, HAVING A LINEAR HYDROCARBON CHAIN OF FROM 5-9 CARBON ATOMS IN POSITION 11

The invention is in the field of estrogenic compounds of the type based on the molecular structure of estradiol. I.e., compounds having a steroidal skeleton the A-ring of which is aromatic, and having a free or capped hydroxyl group at carbon atom No. 3 and at either of carbon atoms Nos. 16 or 17. Estrogenic compounds have a generally recognised utility in the treatment of estrogen-deficiency related disorders, such as menopausal complaints, osteoporosis, and in contraception.

More precisely, the invention pertains to 11β-substituted estradiol derivatives. Such 11β-substituted estradiol derivatives are known from, inter alia, Napolitano et al. in *J. Med. Chem.* 1995, 38, 2774-2779 and Lobaccaro et al. in *J. Med. Chem.* 1997, 40, 2217-2227. From these documents, it can be learned that placing a substituent at the 11β-position may improve the binding affinity for the estrogen receptor, provided that said substituent is not too large. E.g., with an ethynyl group at $C_{11}$ the binding increases, whereas with the next higher homologue, 1-propynyl, it is reported that the binding affinity undergoes a marked drop.

The state of the art in the field of estrogen receptor affinity discriminates between two estrogen receptors, denoted ERα and ERβ, see Mosselman et al., *FEBS Letters* 392 (1996) 49-53 as well as EP-A-0 798 378. Since these receptors have a different distribution in human tissue, the finding of compounds which possess a selective affinity for either of the two is an important technical progress, making it possible to provide a more selective treatment of estrogen-deficiency related disorders, with a lower burden of estrogen-related side-effects.

The present invention is based on the unexpected finding that, despite the above teaching, certain 11β-substituted estradiol derivatives that deviate from those reported by Napolitano et al. possess a surprisingly higher estrogen receptor-affinity. Moreover, the present invention pertains to such 11β-substituted estradiol derivatives as have a selective affinity for both the estrogen receptors ERα and ERβ. By way of preference, the present invention pertains to such 11β-estradiol derivatives as have a specific selective affinity in that these are agonists for ERα and antagonists for ERβ.

To this end, the invention resides in steroid compounds which satisfy the following structural formula I:

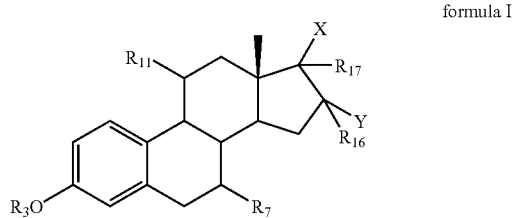

formula I wherein:
one of X and Y is OH, the other being H;
$R_3$ is H, $COR'_3$ with $R'_3$ being alkyl* or aryl;
$R_7$, $R_{16}$, and $R_{17}$ each independently are H, alkyl*, cycloalkyl*, alkenyl*, alkynyl*, aryl;

$R_{11}$ is a hydrocarbon group which may be linear or branched, provided that it comprises one single linear chain having a length of from 5 to 9 carbon atoms as the longest chain on carbon atom no. 11 of the steroid skeleton, wherein said chain may be saturated or unsaturated;

It should be noted that carbon chain length of the groups denoted with an asterisk (*) is not particularly critical, but will generally be up to eight for the aliphatic and alicyclic groups, while aryl generally will be phenyl, pyridinyl, pyrimidyl, which groups can have substitutions customary in the art, such as alkoxy, hydroxy, halogen, nitro, cyano, and amino.

It should be noted that the exact structure of the estrogenic steroid skeleton is not critical as long as the regular requirements of an aromatic A-ring and hydroxyl groups on $C_3$ and $C_{17}$ or $C_{16}$ have been satisfied.

The present invention is directed to the 11β-substitution of such a steroid skeleton. It is the nature of the 11β substitution which has been found to lead to the unexpected effect on estrogen receptor affinity.

The mixed estrogen-receptor profile of the compounds according to the present invention, makes them suitable as improved estrogens, in the sense that they can be used in estrogen-related disorders, such as menopausal complaints and osteoporosis, and in contraception, and further may also be suitable in the treatment or prevention of Alzheimer's disease, breast tumor, benign prostate hypertrophy, and cardiovascular disorders. The preferred compounds of the invention, which have a marked ERα agonistic and ERβ antagonistic profile, are particularly suitable in the treatment and prevention of estrogen-deficiency related disorders under diminished estrogen-related side-effects. The strongly ERβ antagonistic compounds of the invention can also have a utility in the treatment and prevention of endometriosis and other estrogen-related disorders.

As indicated above, the 11β-substituent is a hydrocarbon group comprising a single linear chain having a length of from 5 to 9 carbon atoms. This means that either the main chain of the substituent has a length of from 5 to 9 carbon atoms and any branches have a shorter chain length, or a short group is directly attached to carbon no. 11 of the steroid skeleton as what would normally be regarded as the actual substituent, in which case a side-chain must be present in such a manner that the total number of carbon atoms present in the longest chain attached to carbon atom no. 11 of the steroid skeleton is 5-9.

The number of carbon atoms in the single longest chain according to the invention preferably is lower than 9. More preferably, the number of carbon atoms is 5-7 with 5 or 6 being most preferred. It is further preferred that the 11β-hydrocarbon chain is unbranched, and most preferably contains a double bond or a triple bond.

The 11β-substituent, i.e. $R_{11}$ in formula I preferably is selected from the following group of side-chain structures:

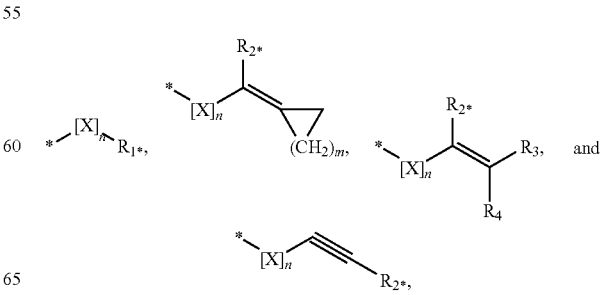

wherein X is $CH_2$, CH-alkyl, or $C(alkyl)_2$, $R_1$ is H, alkyl, $C_3$-$C_7$ cycloalkyl, or together with X forms a $C_3$-$C_7$ ring system, $R_2$ is H, alkyl, or $C_3$-$C_7$ cycloalkyl, $R_3$ and $R_4$ each independently are H, alkyl, or $C_3$-$C_7$ cycloalkyl optionally substituted with halogen or CN, n is an integer of from 0-9, m is an integer of from 1-5.

It is preferred that the further substituent groups denoted in the description of formula I are the following groups:

alkyl is (1-8C) alkyl, meaning a branched or unbranched alkyl group having 1-8 carbon atoms, for example methyl, ethyl, propyl, isopropyl, butyl, sec-butyl, tert-butyl, hexyl and octyl;

cycloalkyl is (3-6C)cycloalkyl meaning a mono- or bicycloalkyl group having 3-6 carbon atoms, e.g. cyclopropyl, cyclobutyl, cyclopentyl, cyclohexyl;

alkenyl is (2-8C)alkenyl, meaning a branched or unbranched alkenyl group having 2 to 8 carbon atoms, such as ethenyl, 2-butenyl, etc.; preferably alkenyl is (3-7C) alkenyl;

alkynyl is (2-8C) alkynyl, which means a branched or unbranched alkynyl group having 2-8 carbon atoms, such as ethynyl and propynyl; preferably alkynyl is (3-7C) alkynyl;

The compounds of the invention may be produced by various methods known in the art of organic chemistry in general, and especially in the art of the chemistry of steroids [see for example: Fried, J. and Edwards, J. A., "*Organic Reactions in Steroid Chemistry*", Volumes I and II, Van Nostrand Reinhold Company, New York, 1972]. The synthesis of the 11β-substituted estradiol derivatives of the invention does not present any special problems to the person of ordinary skill in the art, as is is also evident from the examples given below. The compounds of the invention can also generally be synthesised analogously to the known 11β-substituted estradiol derivatives referred to above.

The present invention also relates to a pharmaceutical composition comprising the steroid compound according to the invention mixed with a pharmaceutically acceptable auxiliary, such as described in the standard reference Gennaro et al., *Remmington's Pharmaceutical Sciences*, (18th ed., Mack publishing Company, 1990, see especially Part 8: Pharmaceutical Preparations and Their Manufacture.). The mixture of the steroid compounds according to the invention and the pharmaceutically acceptable auxiliary may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. nasal spray. For making dosage units, e.g. tablets, the use of conventional additives such as fillers, colorants, polymeric binders and the like is contemplated. In general any pharmaceutically acceptable additive which does not interfere with the function of the active compounds can be used. The steroid compounds of the invention may also be included in an implant, a vaginal ring, a patch, a gel, and any other preparation for sustained release.

Suitable carriers with which the compositions can be administered include lactose, starch, cellulose derivatives and the like, or mixtures thereof used in suitable amounts.

Furthermore, the invention relates to the use of the steroid compound according to the invention for the manufacture of a medicament in the treatment of estrogen-deficiency related disorders such as peri- and/or post-menopausal complaints. Thus the invention also pertains to the medical indications of peri- and/or post-menopausal (climacteric) complaints and osteoporosis, i.e. a method of treatment in the field of HRT (hormone replacement therapy), comprising the administration to a patient, being a woman, of a compound as described hereinbefore (in a suitable pharmaceutical dosage form).

Further, the invention relates to the use of the steroid compound according to the invention in the manufacture of a medicament having contraceptive activity. Thus the invention also pertains to the medical indication of contraception, i.e. a method of contraception comprising the administration to a subject, being a woman or a female animal, of a progestogen and an estrogen as is customary in the field, wherein the estrogen is a compound as described hereinbefore (in a suitable pharmaceutical dosage form).

Finally the invention relates to the use of the steroid compound for the manufacture of a medicament having selective estrogenic activity, such a medicament being generally suitable in the area of HRT (hormone replacement therapy).

The dosage amounts of the present steroids will be of the normal order for estradiol derivatives, e.g. of the order of 0.01 to 10 mg per administration.

The invention is further illustrated hereinafter with reference to some unlimitative Examples and the corresponding formula schemes referred to.

EXAMPLE I

The synthesis of two compounds according to the invention, (10) and (11) in Scheme I is carried out as follows.

2

A mixture of 20 g of 11-butenylestrone 1, 12 ml of ethyleneglycol, 20 ml of triethylorthoformate and 0.5 g of p-toluenesulfonic acid was heated for 2 h. Then the mixture was cooled and poured into sat. aq. $NaHCO_3$. The product was extracted into ethylacetate. After washing, drying and evaporation of the solvent, the crude product was treated with diisopropylether to afford 14 g of 2 as crystalline material; Mp 184-185. $R_f$ 0.58 (heptane/ethyl acetate 6/4).

3

To a solution of 0.5 g of 2 in 10 ml of THF was added 1 ml of dihydropyran, followed by 10 mg of p-toluenesulphonic acid. After stirring for 2 h the mixture was neutralized by addition of 0.5 g of $NaHCO_3$. The mixture was stirred for 15 min. and then poured into water and extracted with ethylacetate. Upon passing the product through a short silica column, 600 mg of 3 was obtained as an oil; $R_f$ 0.75 (heptane/ethyl acetate 6/4).

4

To a solution of 600 mg of 3 in 10 ml of dry THF was added at 0° C. 0.4 ml of 10M $BH_3$.dimethylsulfide complex. After stirring for 1 h all starting material had been consumed. The mixture was carefully treated with 1.6 ml of 10% NaOH and 1.2 ml of 30% aq. $H_2O_2$. After stirring for 4 h the mixture was diluted with water and the product extracted into ethylacetate. Purification by column chromatography provided 470 mg of 4 as a viscous oil; $R_f$ 0.27 (heptane/ethyl acetate 6/4).

5

To a suspension of 17 g of sodium acetate, 35 g of silica gel, and 17 g of pyridiniumchlorochromate in 150 ml of methylene chloride was added a solution of 9.5 g of alcohol 4 in 20 ml of methylenechloride. After stirring the mixture for 1 h, the oxidation was completed and 200 ml of ether and 50 g of Celite was added. The mass was stirred for 15 min and then filtered over a celite path. The residue was concentrated and passed through a short silica gel column, to provide 9.1 g of 5; $R_f$ 0.55 (heptane/ethyl acetate 6/4).

6

To a suspension of 1.3 g of isopropyltriphenylphosphonium bromide in 10 ml of dry THF was added at −30° C. 2.2 ml of a 1.5 M solution of butyllithium in hexane. The mixture was stirred for 15 min. At −30° and for 0.5 h at 0°. Then a solution of 0.47 g of aldehyde 5 in 2 ml of THF was added. After stirring for an additional 1 h at ambient temperature the reaction mixture was poured into water and extracted with ethyl acetate. Chromatography over silica gel, provided 450 mg of 6 as a colorless oil; $R_f$ 0.70 (heptane/ethyl acetate 7/3); starting material $R_f$ 0.46.

7

In a similar way as described above, the related cyclopropylidene derivative 6 was prepared from the aldehyde 5 and cyclopropyltriphenylphosphonium bromide. $R_f$ 0.65 (heptane/ethylacetate 7/3).

8

To a solution of 550 mg of 6 in 10 ml of acetone was added 2 ml of 2N HCl. The mixture was stirred for 1 hr. After neutralization with sat. aq. $NaHCO_3$ the mixture was diluted with water and the product was extracted with ethyl acetate. The material thus obtained was triturated with 70% ethanol, to provide 360 mg of 8 as a white solid; Mp 190-191° C.; $R_f$ 0.43 (heptane/ethyl acetate).

9

In a similar way as described for the related isopropylidene derivative 9 was prepared from the protected material 7 by treatment with 2N HCl; Mp 154-155° C.; $R_f$ 0.38 (heptane/ethyl acetate 7/3).

10

To a solution of 350 mg of 8 in a mixture of 3 ml of THF and 1 ml of abs.ethanol was added 60 mg of sodium borohydride. After stirring for 1 hr excess hydride was destroyed by addition of acetone and after stirring for an additional ½ hr the mixture was diluted with water and the product extracted with ethyl acetate. The product thus obtained was triturated with 60% ethanol, to provide 280 mg of 10; Mp 205-207° C.

11

In an analogous way as described above, reduction of 9 with sodium borohydride afforded the required estradiol derivative 11; Mp 178-179° C.

EXAMPLE II

The synthesis of two further compounds according to the invention, (18) and (21) in Scheme II is carried out as follows.

12

To a solution of 1 g of 3 in 20 ml of dioxane was added 2.8 ml of 2% $OsO_4$ in t-butanol. After stirring this mixture for 10 min. 4 ml of water and 3.4 g of $NaIO_4$ were added. After stirring for 1 h the reaction was complete. The mixture was poured onto water, and extracted with ethyl acetate. After chromatography of the crude product 0.5 g of aldehyde 12 was isolated as an oil; $R_f$ 0.50 (heptane/ethyl acetate 6/4) 0.64; $R_f$ 3: 0.75.

13

A solution of 6.9 g of triphenylphosphine was added at −70° C. to a solution of 4.38 g of tetrabromomethane in 30 ml of dichloromethane. The mixture which had turned orange was stirred additionally for 15 min. at 0° C., and then cooled again to −70° C. A solution of 3 g of steroid 12 in 10 ml of methylene chloride was added and the mixture was stirred for another 1.5 h. The reaction was then poured onto sat. aq. $NaHCO_3$ solution and extracted with dichloromethane. The product thus isolated was purified by chromatography to provide 1.39 g of 13; Mp 163-164° C. (ethanol/water).

14

To a solution of 870 mg of 13 in 10 ml of acetone was added 1.6 ml of 1 N HCl. The mixture was stirred for 2 h. Then the reaction was neutralized by addition of $NaHCO_3$ followed by dilution with 50 ml of water. The product was extracted into ethyl acetate. After drying and concentration 0.70 g of 14 were obtained; $R_f$ 0.60 (heptane/ethyl acetate 6/4).

15

To a solution of 3.7 g of 14 in 20 ml of methanol and 20 ml of THF was added 500 mg of sodiumborohydride. After stirring for 1 h the mixture was poured into 250 ml of sat. aq. $NH_4Cl$ solution and extracted with ethyl acetate. After drying and concentration of the organic phase, the residue was crystallized from ether, to provide 2.7 g of 15; Mp 142-144° C., $R_f$ 0.45 (heptane/ethyl acetate 6/4).

16

To a solution of 2 g of 15 in 40 ml of THF was added 6 ml of dihydropyran, followed by 45 mg of p-toluenesulphonic acid. After stirring for 1½ h the reaction mixture was poured into 200 ml of sat. aq. $NaHCO_3$ solution, and the product was extracted into ethyl acetate, to provide 2.9 g of 16 as an oil; $R_f$ 0.78 (hexane/ethylacetate 6/4)

17

To a solution of 2.9 g of 16 in 50 ml of dry THF was added at −78° C. 6 ml of 1.6M BuLi (in hexane) solution. The mixture was stirred for 30 min. at this temperature. Then 1.4 ml of methyliodide was added and the reaction was allowed to stir for 3 h at −15° C., followed by 3 h at room temperature. After pouring the mixture in 250 ml of water the product was extracted into ethyl acetate, and purification was performed by chromatography over silica gel, to provide 1.4 g of 17 as an oil; $R_f$ 0.38 (heptane/acetone 95/5); $R_f$ 0.71 (heptane/ethylacetate 6/4, starting material $R_f$ 0.78).

18

To a solution of 1.35 g of 17 in 30 ml of a 1/1 mixture of methanol/THF was added 100 mg of p-toluenesulfonic acid. After stirring for ½ h the mixture was poured into 100 ml of sat. aq. $NaHCO_3$ solution and the product was extracted into ethyl acetate. After chromatographic purification 510 mg of 18 was obtained as a white solid; Mp 180-182° C., $R_f$ 0.35 (heptane/ethylacetate 6/4).

19

To a suspension of 2.2 g of cyclopropyltriphenylphosphonium bromide (previously dried over $P_2O_5$ in vacuo at 80° C.) in 30 ml of THF was added at −10° C. 3.2 ml of a 1.6 M BuLi in hexane solution. After stirring for 1 hr at 0° C., a solution of 1.2 g of 12 in 5 ml of THF was added. The mixture was stirred for 1 h at room temperature and then poured into water. Extraction with ethylacetate, followed by chromatography, provided 0.93 g of 19 as an oil; $R_f$ 0.73 (heptane/ethyl acetate 7/3).

20

Deprotection of the ketal and tetrahydropyranyl ether was achieved by stirring 0.45 g of 19 in 10 ml of methanol in the presence of 50 mg of p-toluenesulphonic acid for 2 hr. The reaction mixture was poured into 5% aq $NaHCO_3$ solution and the product was extracted with ethyl acetate. Chromatography provided 120 mg of pure 20; $R_f$ 0.27 (heptane/ethyl acetate 7/3).

Reduction of the 17-keto group was achieved by treatment of a solution of 360 mg of 20 in a mixture of 5 ml of methanol and 5 ml of THF with 80 mg of sodium borohydride. After stirring for 2 h the mixture was poured into 30 ml of sat. aq. NH$_4$Cl solution and the product was extracted with ethyl acetate. Chromatography, followed by trituration with heptane provided 230 mg of 21 as a white solid; Mp 178-179° C. R$_f$ 0.44 (heptane/ethylacetate 6/4).

EXAMPLE III

The compounds of Examples I and II, as well as several other compounds (synthesized in analogous manner) are tested for their estrogenic and anti-estrogenic activity.

Test medium: Intact recombinant CHO cells stably co-transfected with the rat oxytocin promoter and the luciferase reporter gene and either the human estrogen receptor β or the human estrogen receptor α. Both cell lines have been produced within the Department of Biotechnology and Biochemistry (BBC) (N. V. Organon) and are known under the name CHO-ERRO 2B1-1E9 for CHO-ERα and CHO-ERβ RO LUC for CHO-ERβ.

The estrogenic activity of compounds is determined in an in vitro bioassay (CHO-ERα) with recombinant Chinese hamster ovary (CHO) cells stably co-transfected with the human estrogen α (hERα), the rat oxytocin promoter (RO) and the luciferase reporter gene (LUC). The estrogenic activity (potency ratio) of a test compound to promote the transactivation of the enzyme luciferase mediated via the estrogen receptor α is compared with the standard estrogen Org 2317 (estradiol 1,3,5 (10)-estratriene-3,17β-diol). The estrogenic activity (potency ratio) of a test compound to promote the transactivation of the enzyme luciferase mediated via the estrogen receptor β is determined in the same fashion but using recombinant Chinese hamster ovary (CHO) cells stably co-transfected with the human estrogen β (hERβ) (bioassay CHO-ERβ).

The anti-estrogenic activity of compounds is determined in the same bioassays (CHO-ERα and CHO-ERβ), but now the anti-ERα and anti-ERβ activity (potency ratio) of a test compound to inhibit the transactivation of the enzyme luciferase mediated via ERα or ERβ by Org 2317 (estradiol 1,3,5 (10)-estratriene-3,17β-diol) is measured.

The results are presented in the Table below. A rating of the compounds is given in which (−) means that it does not satisfy the ER affinity profile of the present invention, while (+) means a compound according to the invention, i.e. an agonist for ERα and an antagonist for ERβ.

TABLE A

| Compound | ER-α | ER-β | Rating |
| --- | --- | --- | --- |
| 1 | agonist | agonist | − |
| 2 | agonist | agonist | − |
| 3 | agonist | antagonist | + |
| 4 | agonist | agonist | − |
| 5 | agonist | antagonist | + |
| 6 | agonist | antagonist | + |
| 7 | agonist | agonist | − |
| 8 | agonist | antagonist | + |
| 9 | agonist | agonist | − |
| 10 | agonist | agonist | − |
| 11 | agonist | antagonist | + |

TABLE B

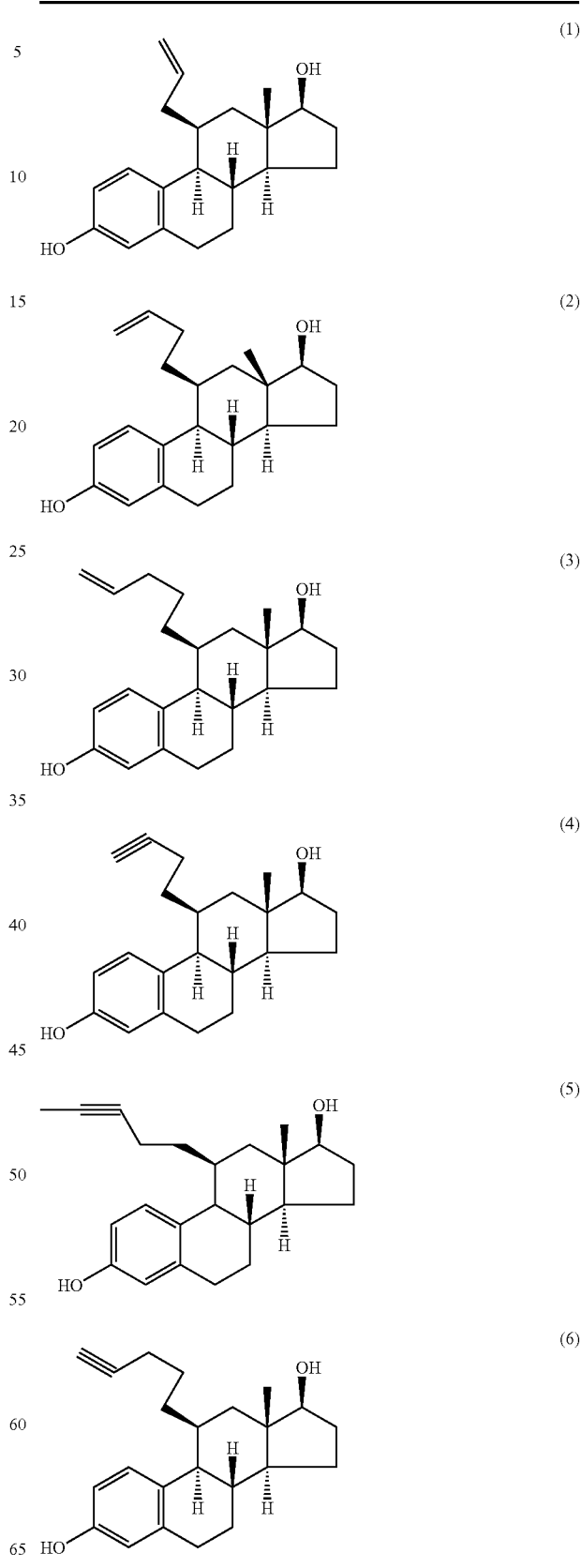

TABLE B-continued
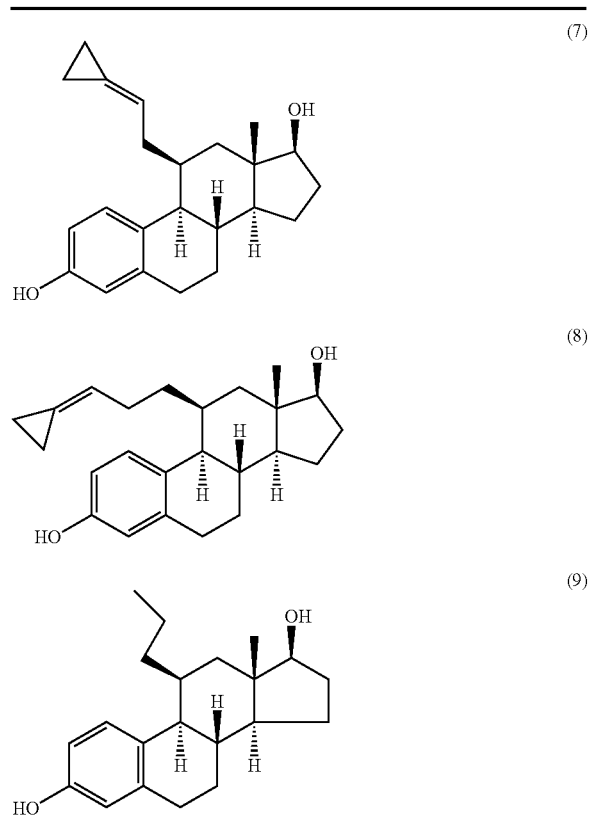
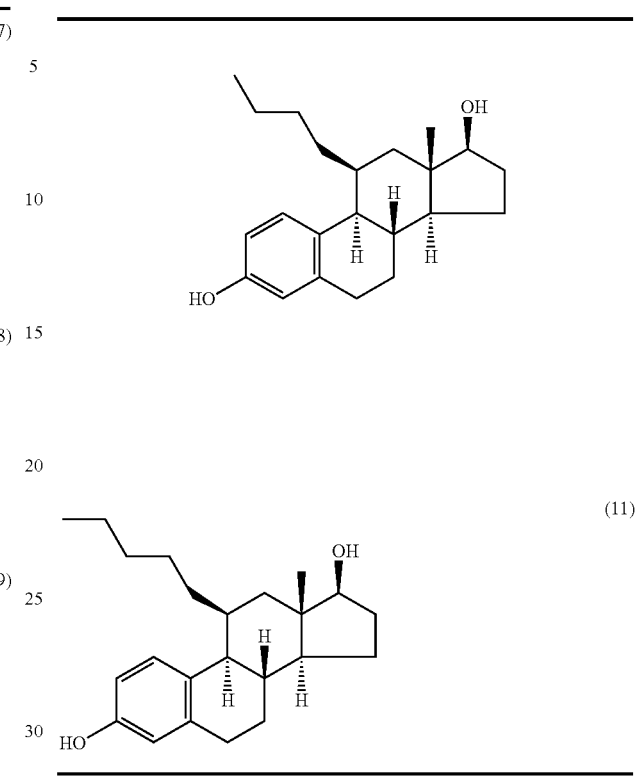
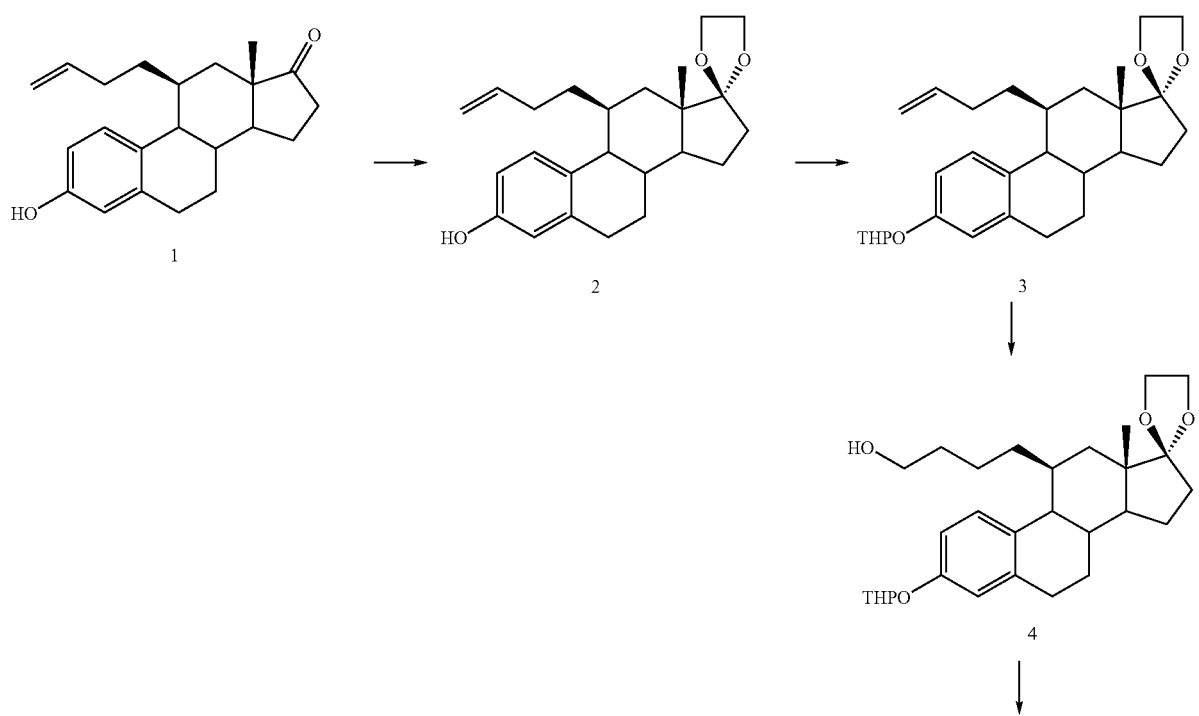

-continued
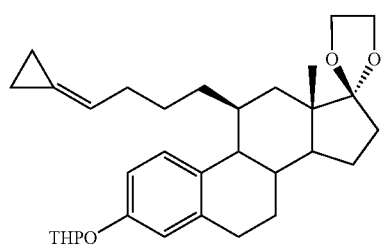
6
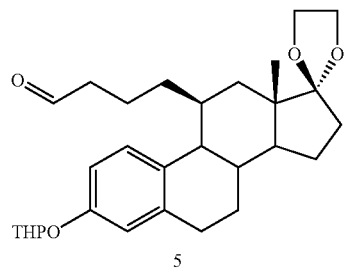
5
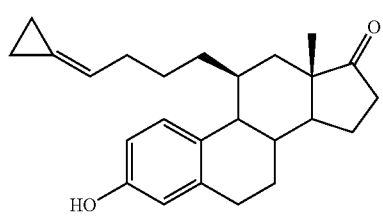
8
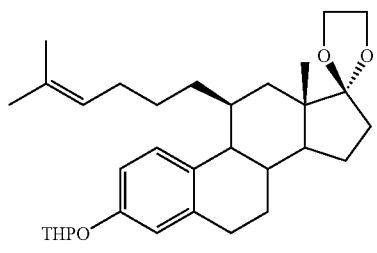
7
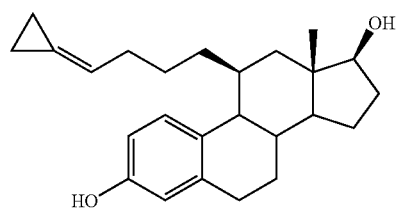
10
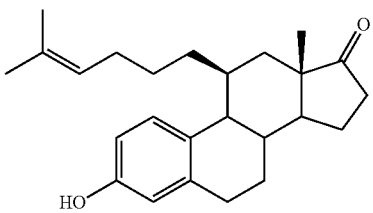
9
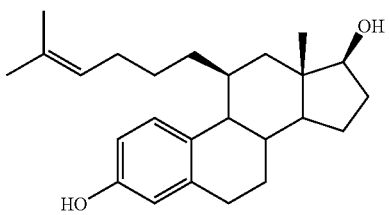
11

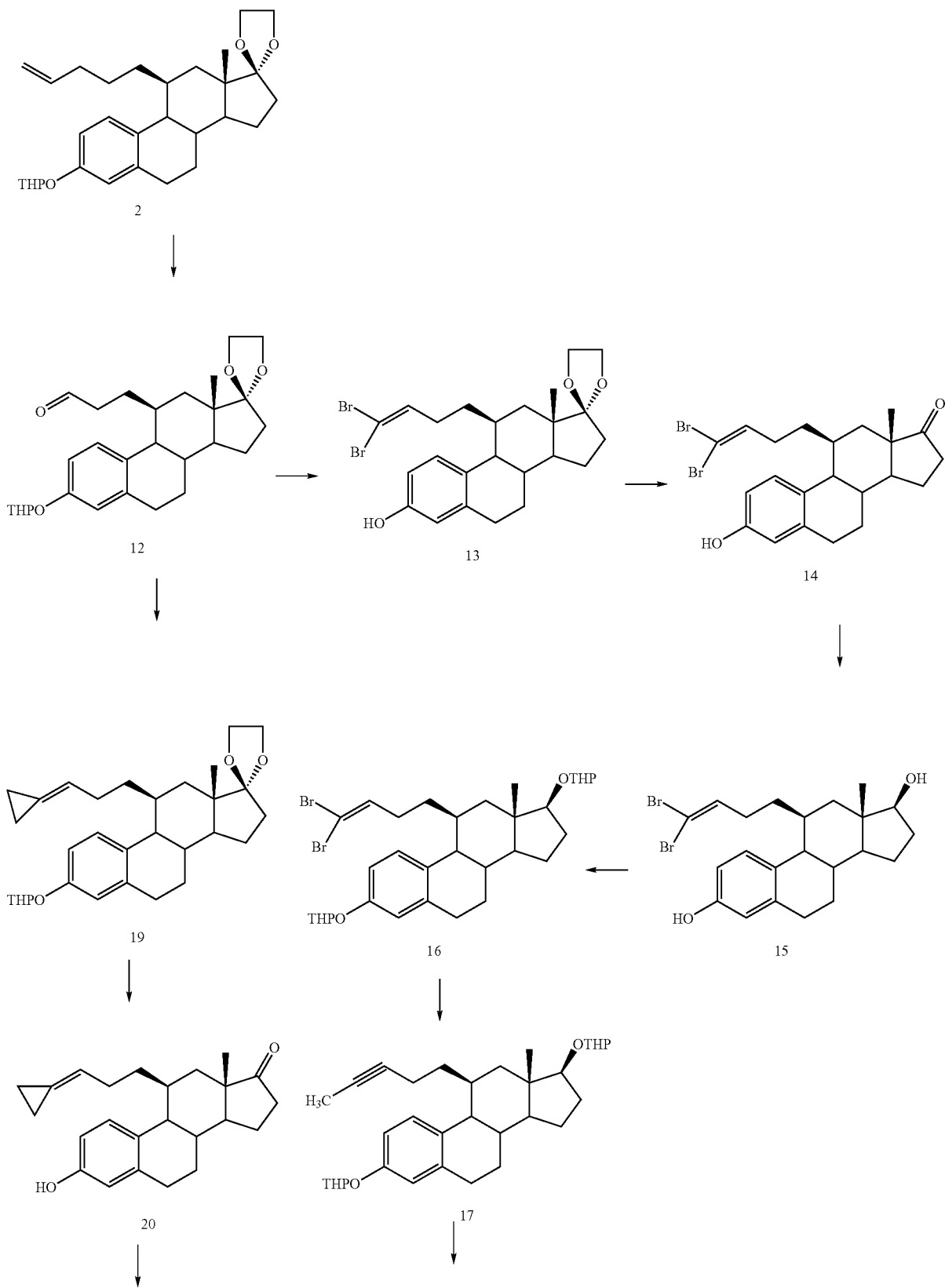
Scheme II

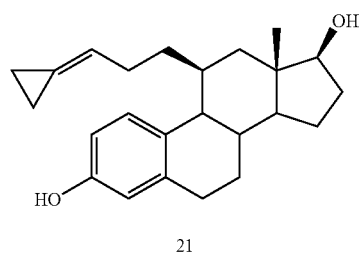

21

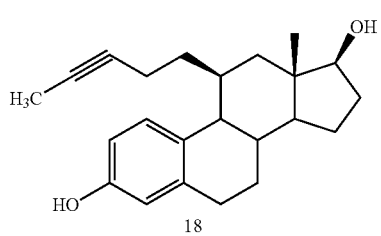

18

The invention claimed is:
1. A pharmaceutical composition comprising:
a steroid compound of the structural formula:

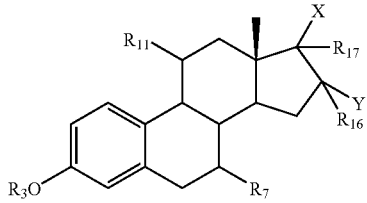

formula I wherein:
one of X and Y is OH, the other being H;
$R_3$ is H or $COR'_3$, with $R'_3$ being alkyl or aryl;
$R_7$, $R_{16}$, and $R_{17}$ each independently are H, alkyl, cycloalkyl, alkenyl, alkynyl or aryl;
$R_{11}$ is selected from the group consisting of

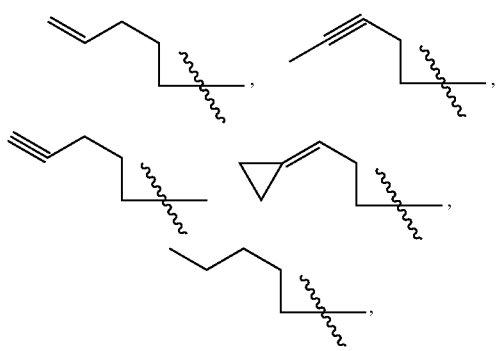

and
a pharmaceutical acceptable auxiliary, wherein the compound of formula I possesses ERα agonist activity and having ERβ antagonist activity.

2. A method for treating estrogen deficiency disorders, comprising:
administering to a patient afflicted with an estrogen deficiency disorder a therapeutically effective amount of the pharmaceutical composition of claim 1.

3. A method of treating estrogen deficiency disorders by inducing ERα agonist activity and ERβ antagonist activity in a patient in need thereof, comprising:
administering a therapeutically effective amount of a steroid compound satisfying the following structural formula:

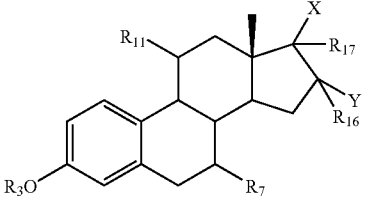

formula I wherein:
one of X and Y is OH, the other being H;
$R_3$ is H or $COR'_3$, with $R'_3$ being alkyl or aryl;
$R_7$, $R_{16}$, and $R_{17}$ each independently are H, alkyl, cycloalkyl, alkenyl, alkynyl or aryl;
$R_{11}$ is selected from the group consisting of

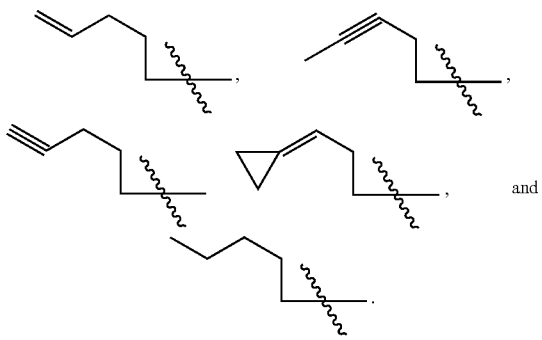

4. A steroid compound of the structural formula:

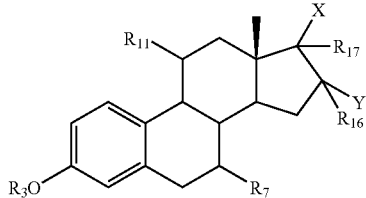

formula I wherein:
one of X and Y is OH, the other being H;
$R_3$ is H or $COR'_3$, with $R'_3$ being alkyl or aryl;
$R_7$, $R_{16}$, and $R_{17}$ each independently are H, alkyl, cycloalkyl, alkenyl, alkynyl or aryl; $R_{11}$ is selected from the group consisting of

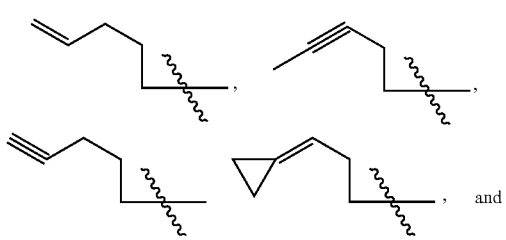
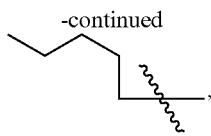
wherein the compound of formula I possesses ERα agonist activity and ERβ antagonist activity.
* * * * *